US00PP16994P3

(12) United States Plant Patent
Lim

(10) Patent No.: US PP16,994 P3
(45) Date of Patent: Aug. 15, 2006

(54) SHRUB ROSE PLANT NAMED 'BAIOON'

(50) Latin Name: *Rosa hybrida*
Varietal Denomination: BAIoon

(75) Inventor: Peter P. Lim, Yamhill, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 89 days.

(21) Appl. No.: 11/014,953

(22) Filed: Dec. 20, 2004

(65) Prior Publication Data

US 2006/0137047 P1 Jun. 22, 2006

(51) Int. Cl.
*A01H 5/00* (2006.01)

(52) U.S. Cl. ..... Plt./104

(58) Field of Classification Search ..... Plt./104, Plt./111

See application file for complete search history.

*Primary Examiner*—Kent Bell
*Assistant Examiner*—June Hwu
(74) *Attorney, Agent, or Firm*—Buchanan Ingersoll PC

(57) ABSTRACT

A new and distinct variety of landscape shrub rose plant is provided which forms on a recurrent basis attractive large fully double medium yellow quartered blossoms that change to light lemon yellow upon maturity. The plant exhibits a dense upright shrub or climbing growth habit depending upon the zone where grown. The dark green glossy foliage contrasts nicely with the yellow blossom coloration. High tolerance to Black Spot and Powdery Mildew is displayed. The plant can be grown to advantage to provide attractive ornamentation in parks and gardens.

3 Drawing Sheets

Botanical commercial classification: *Rosa hybrida*/Shrub Rose Plant.

Varietal denomination: cv. BAIoon.

SUMMARY OF THE INVENTION

The new variety of *Rosa hybrida* landscape shrub rose plant was created at Yamhill, Oreg., U.S.A., during 1996 by artificial pollination wherein two parents were crossed which previously had been studied in the hope that they would contribute the desired characteristics. The female parent (i.e., the seed parent) was a hybrid *Rosa hybrida* shrub rose designated 'R871' (non-patented in the United States). The male parent (i.e., the pollen parent) was the 'POUlurt' (variety U.S. Plant Pat. No. 9,637). The 'POUlurt' variety sometimes is known as the 'Aspen' variety. The parentage of the new variety can be summarized as follows:

'R871'×'POUlurt'.

The seeds resulting from the above pollination were sown and plants were obtained which were physically and biologically different from each other. Selective study resulted in the identification of a single plant of the new variety having the distinctive ornamental characteristics hereafter described.

It was found that the new variety of the present invention:

(a) exhibits a dense upright shrub or climbing growth habit depending on the zone where grown, (b) forms on a recurrent basis attractive large fully double medium yellow quartered blossoms that change to light lemon yellow upon maturity, (c) forms dark green glossy foliage, (d) displays high tolerance to Black Spot and Powdery Mildew, and (e) is particularly well suited for growing as attractive ornamentation in parks and gardens.

In cooler regions, the new variety is an upright and bushy shrub and in warmer zones it is a climber. The medium yellow buds open to a full bloom with shades of medium to pale yellow. The center petals tend to retain a darker shade while the outer petals fade to a light lemon yellow. Finally, the entire bloom becomes mostly light yellow. The blossom coloration contrasts nicely with the glossy dark green foliage. The new variety performs well in U.S.D.A. Hardiness Zone Nos. 4 to 9.

The new variety well meets the needs of the horticultural industry. It can be grown to advantage where attractive ornamentation is desired, such as in parks and gardens.

The new variety can be readily distinguished from other varieties including its parental varieties. More specifically, the 'R871' parent forms light yellow blossoms having approximately 15 petals, and medium green foliage. The 'POUlurt' parent forms yellow blossoms having approximately 15 to 25 slightly ruffled petals, and medium green semi-glossy foliage.

The new variety of the present invention also can be readily distinguished from the 'Prairie Harvest' variety (non-patented in the United States) and the 'MORyelrug' variety (U.S. Plant Pat. No. 6,793). Both of these varieties form lighter green foliage and significantly larger blossoms having substantially lesser petal counts.

The new variety has been found to undergo asexual propagation by budding on an understock beginning in August 1997 and by the rooting of cuttings. 'Dr. Huey' rootstock (non-patented in the United States) was used during the budding. Such asexual propagation by these techniques at Yamhill, Oreg., U.S.A., St. Paul, Minn., U.S.A., and at Phoenix, Ariz., U.S.A., has shown that the characteristics of the new variety are stable and are strictly transmissible by such asexual propagation from one generation to another. Accordingly, the new variety reproduces true to type. The new variety grows well on its own roots.

Initially the new plant was designated '96R405', and was evaluated during 2002 and 2003 under the designation '02R513'. The new variety subsequently has been named the 'BAIoon', and currently is being marketed while using the TAHITIAN MOON and LIFESTYLE GARDEN trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors at St. Paul, Minn., U.S.A. and Yamhill, Oreg., U.S.A. during the 2003 and 2004 seasons.

DETAILED DESCRIPTION

Figure 1:
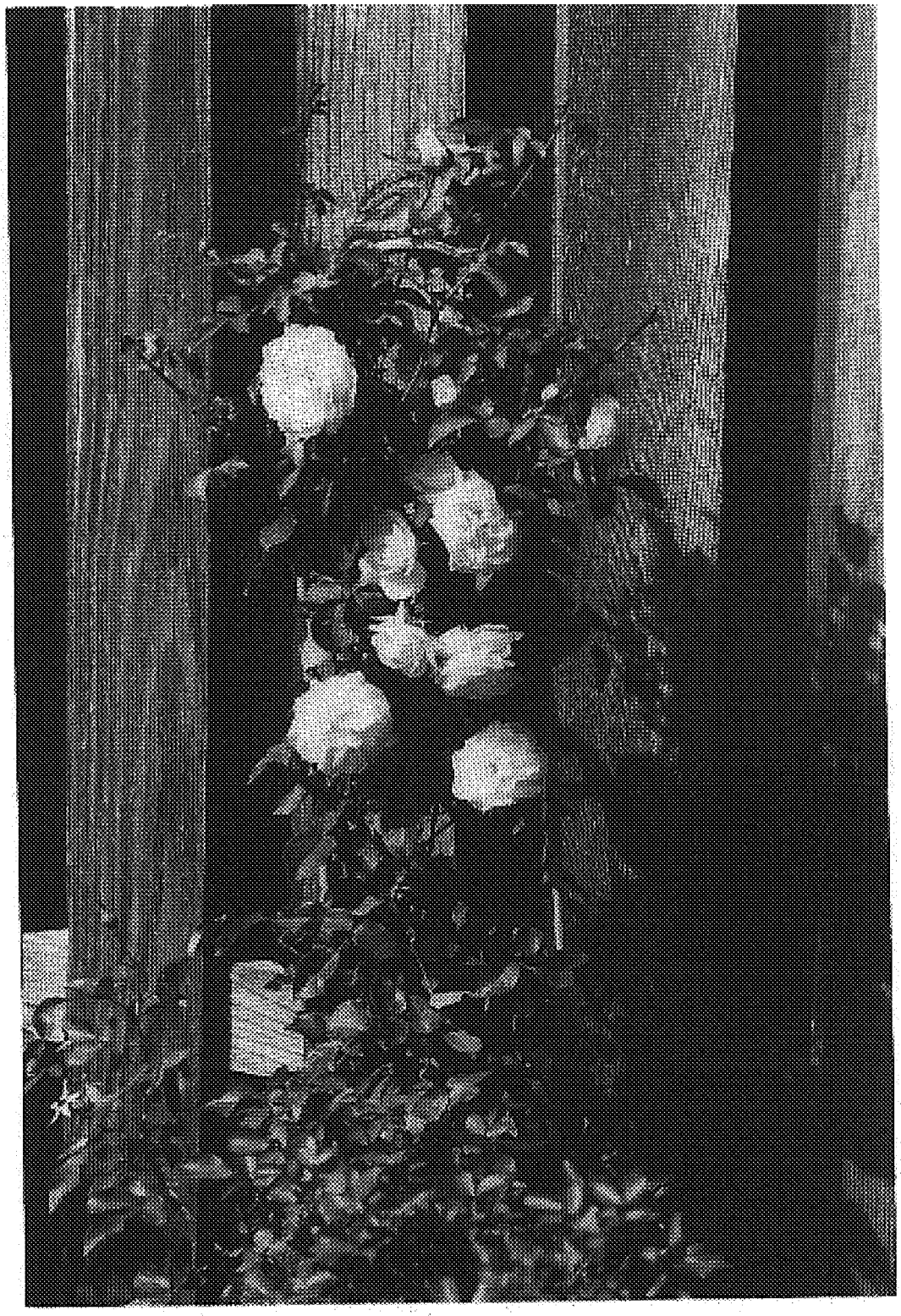
FIG. 1 illustrates a flowering plant of the new variety while present on a support. The attractive glossy dark green foliage is shown to contrast well with the very double yellow blossoms.
Figure 2:
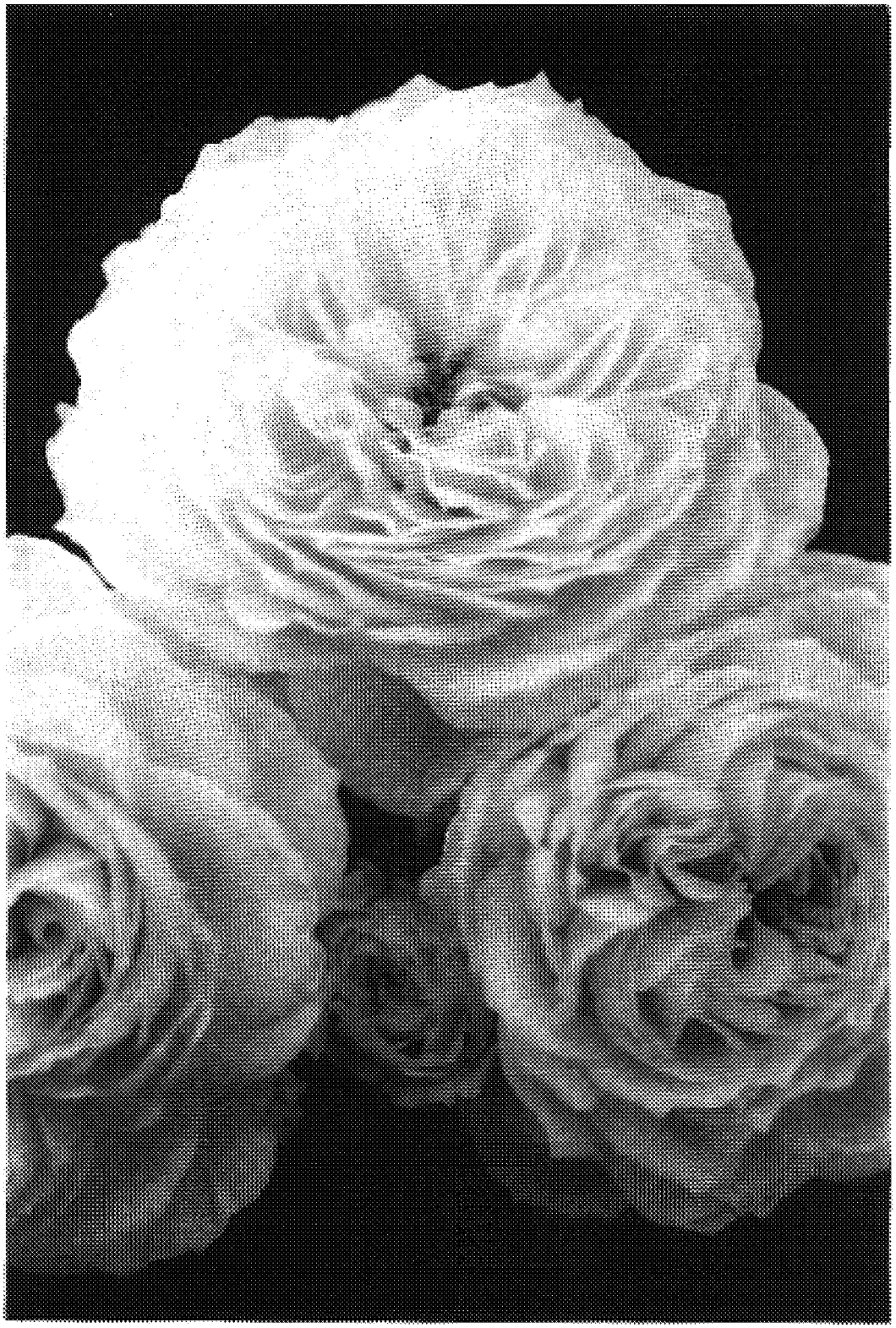
FIG. 2 illustrates a close view of the several very double blossoms wherein the typical quartered arrangement of the petals is illustrated.
Figure 3:
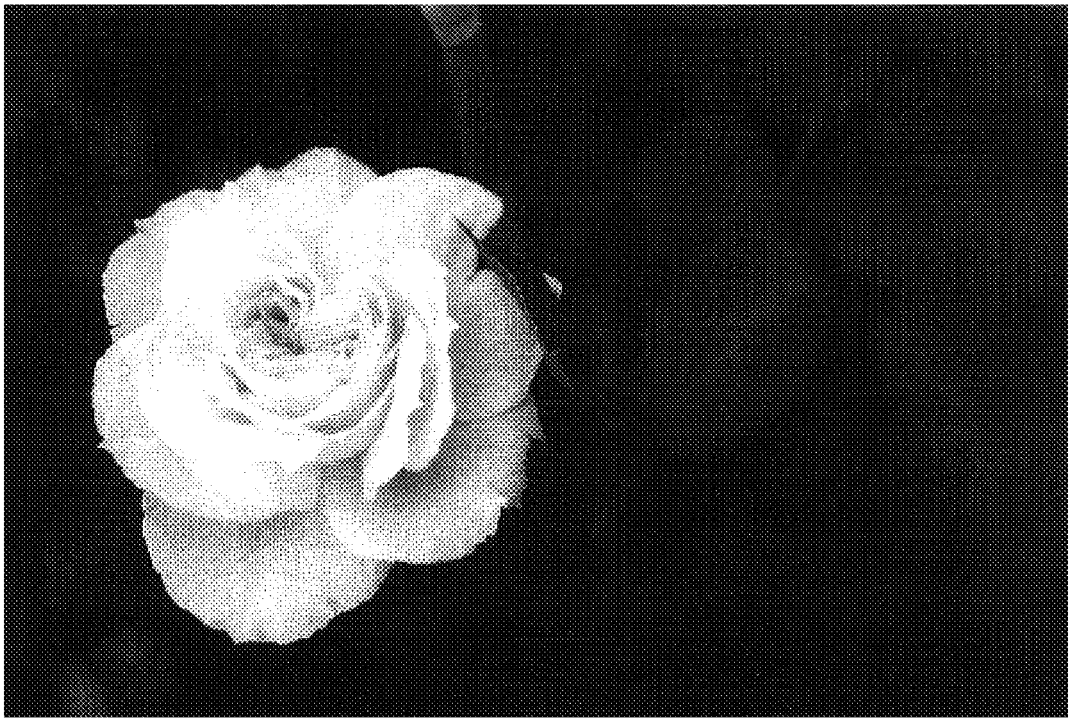
FIG. 3 illustrates a close view of a typical blossom during the course of opening as well as foliage.
Figure 4:
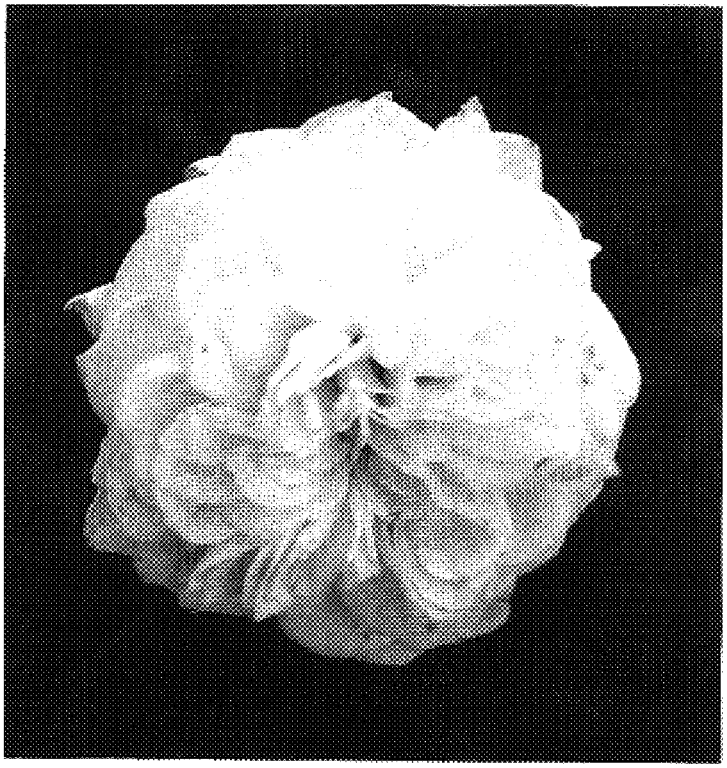
FIG. 4 illustrates a further close view of a fully mature blossom of the new variety.

The chart used in the identification of the colors is that of The Royal Horticultural Society (R.H.S. Colour Chart). Common color terms are to be accorded their ordinary dictionary significance. The description is based on the observation of three and four year-old plants while grown outdoors on their own roots during June 2003 at Yamhill, Oreg., U.S.A., and July 2004 at St. Paul, Minn., U.S.A.

Botanical classification: *Rosa hybrida,* var. 'BAIoon'.
Class: Landscape Shrub.
Plant:
- *Height.*—Approximately 60 cm to 1.8 m on average at the end of the growing season.
- *Width.*—Approximately 55 cm to 1.25 m on average at the end of the growing season.
- *Habit.*—Dense upright shrub in the cooler climates, and a climber in warmer climates.

Branches:
- *Color.*—Young stems: Yellow-Green Group 144B. Adult wood: Greyed-Green Group 197B with streaks of Grey-Brown Group 199C and 199D.
- *Texture.*—Young stems: glabrous. Adult stems: rough with bark-like ridges.
- *Thorns.*—Size: commonly approximately 10 mm in length on average. Shape: triangular to slightly hooked. Quantity: approximately 3 on average over a branch length of 5 cm. Color: Yellow-Green Group 144B and 144C with highlights of Greyed-Purple Group 185C.

Leaves:
- *Size.*—Length: approximately 10.1 cm on average. Width: approximately 7.5 cm on average.
- *Stipules.*—Generally parallel with the auricle facing outward, approximately 1.6 cm in length on average, approximately 4.1 mm in width on average, and Yellow-Green Group 144A in coloration commonly with some Yellow-Green Group 144B on ridges on either side of a central ridge.
- *Petioles.*—Upper surface: Yellow-Green Group 144A. Under surface: Yellow-Green Group 144B and 144C. Length: approximately 2.1 cm on average. Diameter: approximately 1 mm on average. Texture: generally glabrous with a few spines on both sides.
- *Leaflets.*—Number: 3, 5 (most often), and 7. Size: approximately 4.5 cm in length on average, and approximately 2.8 cm in width on average. Shape: obovate to elliptic with a rounded base and an acuminate tip. Margin: serrulate. Texture: bears a glossy finish. General appearance: dark green with a glossy surface when mature. Color (young foliage): Upper surface: Yellow-Green Group 147A tinted with Greyed-Purple Group 185A. Under surface: Yellow-Green Group 147A tinted with Greyed-Purple Group 184C. Color (adult foliage): Upper surface: Yellow-Green Group 147A. Under surface: Yellow-Green Group 147B.

Inflorescence:
- *Number of flowers.*—Typically in clusters, and commonly approximately 3 flowers on average per stem.
- *Peduncle.*—Glabrous, medium stiff, commonly approximately 7.15 cm in length on average, and Yellow-Green Group 144A and 144B in coloration.
- *Sepals.*—Upper surface: Green Group 143A with pubescence. Under surface: Yellow-Green Group 144A streaked with Green Group 143A. Size: approximately 1.25 cm in length on average. Shape: upright at the bud stage, generally horizontal when opening, and reflexed when in full bloom. Apex: initially apiculate, and then may grow a small leaf-shaped appendage with a main vein. Texture: tomentose on the upper surface and glabrous on the under surface. Foliaceous appendages: commonly present on three sepals with one or two appendages on each side which are approximately 4.5 mm in length with a pointed apex and ciliate margin.
- *Buds.*—Shape: generally globose. Size: medium. Length: approximately 3.5 cm on average. Diameter: approximately 2.0 cm on average. Color: Upper petal surface: Yellow Group 7A. Under petal surface: Yellow Group 7A.
- *Flower.*—Form: fully double. Diameter: approximately 6.5 cm on average. Color (when opening begins): Upper surface: Yellow Group 6A lightening to Yellow Group 4D at the margin. Under surface: Yellow Group 6A lightening to Yellow Group 6D at the margin. Color (when blooming): Upper surface: Yellow Group 6C lightening to Yellow Group 4C and 4D at the margin with the inner petals being Yellow Group 6B and 6C lightening to Yellow Group 8C. Under surface: Yellow Group 5D blended with Yellow Group 6D lightening to Yellow Group 4D, and to Yellow Group 5D and Yellow Group 6D on the outer petals. Color (at end of blooming): Upper surface: commonly between Yellow Group 8B and 8C with some lightening to Yellow Group 4D. Under surface: commonly between Yellow Group 8C and 8D. Color (basal petal spot): Yellow Group 9A. Fragrance: slight rose. Lasting quality: the blossoms commonly last approximately 5 to 8 days on average depending upon the temperature and sunlight exposure. Petal number: commonly approximately 95 to 115 on average. Petal shape: orbicular with a point at the apex. Petal size: approximately 3.7 cm in length on average, and approximately 3.4 cm in width on average. Petal texture: glabrous, smooth and satiny.

Petal drop: commonly the petals detach cleanly at full blossom maturity. Stamen number: commonly approximately 56 on average. Anthers: Yellow Group 9B, approximately 3 mm in length on average, and approximately 1.5 mm in width on average. Filament color: Yellow Group 12B. Filament length: approximately 1 cm on average. Pollen: Yellow Group 13A. Pistils: approximately 71 on average. Stigmas: Yellow Group 10C blending to Orange-Red Group 34B, approximately 1.3 mm in length on average, and approximately 1 mm in width on average. Style color: Yellow Group 2C. Style length: approximately 6.7 mm on average. Receptacle: when the flower is fully open is urn-shaped, approximately 8 mm in height, approximately 5.6 mm in diameter, and the coloration commonly is Yellow-Green Group 144A and 144B with some Greyed-Purple Group 184B on the side exposed to the sun. Hips: glabrous, obovate in configuration, approximately 2.5 cm in length, approximately 1.5 cm in width, and Yellow-Green Group 144A mottled with Yellow-Green Group 144B in coloration. Seeds: medium beige in coloration, and approximately 3 mm in length.

Development:

*Vegetation.*—Vigorous.

*Blooming.*—Recurrent.

*Resistance to diseases.*—Highly tolerant to Black Spot and Powdery Mildew.

*Hardiness zone.*—U.S.D.A. Hardiness Zone Nos. 4 to 9.

I claim:

1. A new and distinct landscape shrub rose plant characterized by the following combination of characteristics:

(a) exhibits a dense upright shrub or climbing growth habit depending upon the zone where grown, (b) forms on a recurrent basis attractive large fully double medium yellow quartered blossoms that change to light lemon yellow upon maturity, (c) forms dark green glossy foliage, (d) displays high tolerance to Black Spot and Powdery Mildew, and (e) is particularly well suited for growing as attractive ornamentation in parks and gardens;

substantially as herein shown and described.

* * * * *